United States Patent [19]

Strandberg et al.

[11] Patent Number: 5,500,005
[45] Date of Patent: Mar. 19, 1996

[54] ACTIVITY RESPONSIVE HEART STIMULATOR DEPENDENT ON RETURN BLOOD FLOW TO THE HEART

[75] Inventors: Hans Strandberg, Sundbyberg; Kurt Hoegnelid, Vaesterhaninge, both of Sweden

[73] Assignee: Pacesetter AB, Solna, Sweden

[21] Appl. No.: 271,717

[22] Filed: Jul. 7, 1994

[30] Foreign Application Priority Data

Jul. 7, 1993 [SE] Sweden .................................. 9302358

[51] Int. Cl.$^6$ ........................................................ A61N 1/39
[52] U.S. Cl. ............................................................ 607/17
[58] Field of Search ...................................... 607/9, 19, 24

[56] References Cited

U.S. PATENT DOCUMENTS 4,535,774  8/1985  Olson .

FOREIGN PATENT DOCUMENTS

| 0310026A2 | 4/1989 | European Pat. Off. . |
| 0474958A2 | 3/1992 | European Pat. Off. . |
| 0503839A2 | 9/1992 | European Pat. Off. . |
| 0591642A1 | 4/1994 | European Pat. Off. . |
| WO93/02745 | 2/1993 | WIPO . |

OTHER PUBLICATIONS

"Halbleiterbildaufnehmer für die Röntgentechnik," Rozière et al, Elektronik, vol. 17, No. 22 Aug. 1986 (pp. 62–66).

*Primary Examiner*—William E. Kamm
*Assistant Examiner*—Marianne Parker
*Attorney, Agent, or Firm*—Hill, Steadman & Simpson

[57] ABSTRACT

A heart stimulator emits stimulation pulses to a heart, and has a regulator unit for regulating a variable function in the heart stimulator, a measurement device for measuring the return flow of blood to the heart, and a control device for controlling the regulation of the function by the regulator unit on the basis of changes in the return flow of blood. The regulator unit may be a pulse generator which generates and emits the stimulation pulses at a variable interval, the heart stimulator then becoming rate-adaptive and optimizing cardiac output. In this manner, heart rate is regulated on the basis of a variable directly related to the body's oxygenation needs.

20 Claims, 3 Drawing Sheets

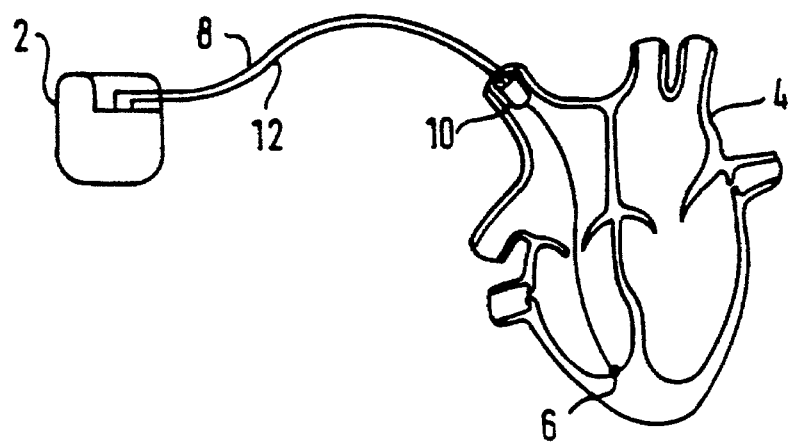
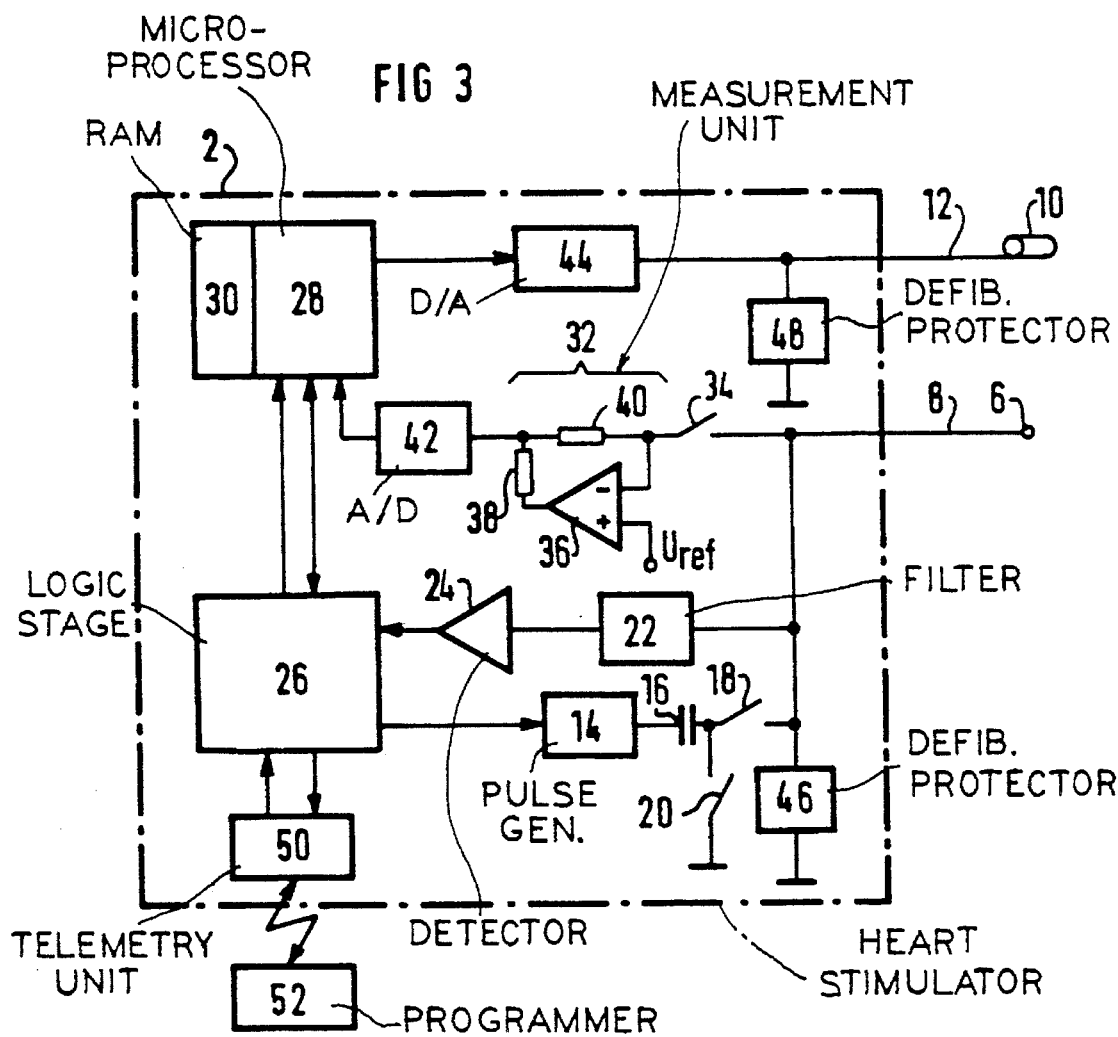

ACTIVITY RESPONSIVE HEART STIMULATOR DEPENDENT ON RETURN BLOOD FLOW TO THE HEART

BACKGROUND OF THE INVENTION

1. Field of the Invention

The present invention relates to a heart stimulator of the type having at least one regulator unit for regulating a variable function in the heart stimulator, a measurement device for measuring an activity-related physiological variable, and a control device for controlling the regulation of the function by the regulator unit on the basis of the physiological variable.

2. Description of the Prior Art

The task of a heart stimulator is to stimulate a defective or dysfunctional heart. In order to provide the patient with an optimum quality of life, the heart stimulator should supply the defective heart with therapy producing a cardiac function as closely resembling the function of a healthy heart as possible. In order to achieve this, the heart stimulator must perform a number of functions, such as determining the amplitude and duration of stimulation pulses, the interval at which stimulation pulses are to be emitted, whether both the atrium and ventricle are to be stimulated, the interval to elapse between an atrial and a ventricular stimulation pulse, etc.

The stimulation interval is a particularly important parameter for the heart stimulator. By changing the stimulation interval, the heart rate can be varied and induced to simulate the rate variations occurring in a healthy heart during e.g., activity or stress. A number of known heart stimulators have been devised which attempt to simulate the response of a healthy heart to activity.

One such prior art heart stimulator is described in U.S. Pat. No. 4,535,774 in which the stroke volume of a heart is determined either by measuring blood flow into the heart or by measuring impedance in the heart. The stroke volume determined in this manner is used to set a stimulation rate to achieve the most optimum cardiac function possible, i.e., to make the amount of blood pumped out the heart each minute sufficient for the body's needs without the heart rate becoming excessively fast. A relationship between stroke volume and heart rate is utilized for this purpose in which stroke volume is assumed to increase with increasing heart rate.

Thus, this known heart stimulator actually measures the heart's stroke volume and then uses changes in this parameter for determining an appropriate stimulation rate which is then imposed on the heart.

The utilization of stroke volume, however, is not an especially suitable way of controlling the heart rate because of the heart's physiological operation and the normal course of a cardiac cycle.

Human blood distributed between two divisions of the circulatory system. The pulmonary division carries blood low in oxygen from the right half of the heart to the lungs for oxygenation and thereafter to the left half of the heart. The systemic division carries oxygenated blood from the left half of the heart, distributes it to body tissue in order to supply same with oxygen, among other things, and returns the blood to the right half of the heart. The veins which return blood to the heart in the systemic division constitute a reservoir for blood and hold most of the body's blood at any given time (about 60% when the body is at rest). The volume of blood pumped each minute in the respective division is referred to as cardiac output. During exertion, stress or the like, cardiac output increases and, accordingly, the flow of blood through arteries and veins also increases. In the arteries the increase of blood flow results in an increase in blood pressure. Pressure does not change much in the veins, however, since venous walls are elastic and stretch when a larger flow of blood must pass. The actual rate of flow, however, does vary.

In principle, the cardiac cycle comprises two phases, a blood-failing phase (diastole) and a blood-emptying phase (systole). Diastole begins with relaxation of atrial heart tissue. Blood then flows into the atria which at the time serve as transient blood reservoirs. Ventricular muscle tissue then relaxes, and the valves between the heart's atria and ventricles open to admit blood into the ventricles. When the ventricles have filled with blood, systole commences with an atrial contraction forcing an additional charge of blood, which can amount to about ⅓ of the total capacity of the ventricles in a healthy person, into the ventricles. When the flow of blood from the atria into the ventricles ceases, the heart valves close, and the ventricles contract to pump blood into the respective circulations divisions. Atrial diastole starts once again during the ventricles' contraction phase.

In principle, the ventricles have a specific maximum volume capacity. Stroke volume can then vary depending on how strongly the ventricles contract, i.e., on the amount of blood remaining in the ventricles at the end of systole. Cardiac output can therefore increase during exertion when both stroke volume and heart rate increase. Most of the increase in cardiac output, however, occurs by means of an increase in heart rate. During excessively fast heart rates, however, the stroke volume can decrease, since the return flow of blood to the heart then does not have time to achieve adequate blood-filling.

When a heart is defective or damaged, the rate at which it beats can be too slow. The return flow of blood to the heart can also be impaired when the atrium and ventricle contract asynchronously. As noted above, the atria contribute about ⅓ of the ventricular blood volume in each heart cycle. Stroke volume thus can be badly affected if the atria and ventricles are not correctly synchronized. A control function which sets a stimulation rate on the basis of changes in stroke volume, as described for the aforementioned known heart stimulator, is therefore inappropriate for persons having a defective cardiac function.

In European Application 0 591 642, a rate-adaptive heart stimulator is described which utilizes the degree of blood-filling of the heart in determining the stimulation point in time. The degree of blood-filling can be determined by measuring blood flow or by measuring impedance in the heart. The flow of blood into the ventricles ceases at the end of the blood-filling phase, and a threshold value can be established which corresponds to an adequate degree of blood-filling. Impedance designates, in the corresponding manner, the degree of filling of the heart.

SUMMARY OF THE INVENTION

An object of the present invention is to provide a heart stimulator which effectively optimizes different functions in the heart stimulator. In particular, the invention aims to achieve a heart stimulator which optimizes cardiac output.

Such heart stimulator is obtained in accordance with the invention wherein a physiological measurement device measures the return flow of blood to the heart, and a control device controls the regulator unit's regulation of the regulated function on the basis of changes in the measured return flow of blood.

One advantageous way of measuring the return flow of blood is achieved in accordance with the invention in an embodiment wherein the measurement device is connected to a first electrode and a second electrode, and a voltage supply is connected to maintain a constant voltage across the electrodes, whereby current from the measurement device corresponds to blood return.

In (as yet) unpublished European Patent Application No. 94100130.7, a flow meter is described which operates in this way and which is suitable for use in conjunction with the present invention.

As noted above, the main object of the invention is to produce a rate-adaptive heart stimulator which optimizes cardiac output. This is achieved in an embodiment wherein the regulator unit comprises a pulse generator for generating and emitting stimulation pulses to the heart at a variable stimulation interval.

The return flow of blood to the heart through the veins depends on the return flow of blood from the tissues to the veins. This can be viewed as the active circulation of blood to accommodate the body's needs, i.e., the replacement of blood expended by tissue. The function of the heart, according to this view, is then to pump this volume of blood efficiently through the circulatory systems and maintain the pressure difference between arteries and veins. As the return flow of blood is governed by the body's need for oxygen, an optimum stimulation rate and cardiac output are obtained when the heart can just pump out the return flow of blood without impeding it. Since the atria serve as reservoirs for blood pumped into the ventricles, the return flow of blood to the heart is preferably measured in the vena cava.

In a further embodiment of the invention the heart stimulator further comprises an averager for determining the average value for the return flow of blood to the heart as measured by the measurement device; the control device then controls the pulse generator's stimulation interval on the basis of changes in the determined average value.

Since there are variations in the return flow of blood during the heart cycle and between heart cycles, controlling the stimulation interval on the basis of changes in an average value for the return flow of blood is advantageous. This will also keep the stimulation interval from changing too rapidly.

One way of determining the average value is achieved in an embodiment wherein the averager comprises means for sampling a predetermined number of measured values for the return flow of blood in each heart cycle, and the averager determines the average value for the return flow of blood in a predetermined, preceding time interval, or a predetermined number of preceding heart cycles, on the basis of the sampled measurement values. In principle, the number of sampled measurement values can range from one sample per heart cycle to any optional number of samples per heart cycle.

One alternative way of determining the average value is achieved in an embodiment wherein the averager comprises a means for determining the maximum value and minimum value for the return flow of blood in each heart cycle and the averager determines the average value for a predetermined number of previous heart cycles on the basis of the determined maximum and minimum values.

A third alternative is achieved in another embodiment wherein the averager determines the average value for the continuous measurement signal for the return flow of blood for a predetermined, preceding time interval, or a predetermined number of preceding heart cycles. One way of obtaining continuous averaging of the measurement signal is achieved by subjecting the measurement signal to low-pass filtering for the predetermined number of preceding heart cycles.

Another function in the heart stimulator can be controlled in accordance with the invention in an embodiment wherein the heart stimulator is devised so a first tip electrode is placed in an atrium of the heart and a second tip electrode is placed in a ventricle of the heart in order to deliver atrial and ventricular stimulation pulses respectively to the heart, the regulator unit includes a timer for regulating a variable time interval between delivery of atrial stimulation pulses and delivery of ventricular stimulation pulses and the control device controls the timer's timing interval.

When both the atrium and ventricle are stimulated by the heart stimulator, the time elapsing between the atrial stimulation pulse and the ventricular stimulation pulse, i.e., the A–V interval, will affect the efficacy of cardiac function. As noted above, a heart operating asynchronously can lose about ⅓ of the maximum capacity of the ventricle. When the A–V interval is regulated on the basis of the measured return flow of blood, an optimum A–V interval can be set which produces the most efficient pumping operation for the heart.

Other heart stimulator functions which can be similarly controlled on the basis of the measured return flow of blood are refractory times and the effect of other sensors on the stimulation interval. Other sensors could e.g., sense the body's acceleration or metabolic parameters, such as blood temperature and blood oxygen content.

It is advantageous if the heart stimulator comprises a means for monitoring changes in the return flow of blood measured by the measurement device, and if a momentary change in blood flow, occurring in a predetermined time interval, exceeds a predetermined threshold value it is interpreted as abnormal and ignored by the control device during control of the function unit's regulation of the function.

This would, e.g., keep asynchronous atrial contractions from affecting determination of the stimulation interval. An atrial contraction coinciding with the ventricular contraction would prevent blood in the atrium from being pumped into the ventricle, since the heart valve would then be closed. Blood would therefore be pumped back into the circulation and affect blood return through the veins, causing so-called cannon waves.

An additional refinement of the heart stimulation is achieved in accordance with the invention in an embodiment wherein the heart stimulator further includes a memory unit for storing values representing the return flow of blood over a predetermined period of time, preferably at least 24 hours.

When values for the return flow of blood are stored either in the form of average values for flow, i.e., the actual flow, or variations in flow over a long period of time, e.g., at least 24 hours, the measurement device can be compensated for long-term component drift during measurements. Other correction factors can also be set on the basis of statistics stored relative to the return flow of blood. The memory unit can be devised so it exclusively stores the minimum value and the maximum value (updated in a running basis) for the predetermined period of time.

It is advantageous if the memory unit is devised to also store values representing stimulation intervals for the aforementioned predetermined period of time. The control device then can calculate, on the basis of the stored values for the return flow of blood and stimulation intervals, the way in which the return flow of blood varies with changes in the stimulation interval and, on the basis thereof, can determine how the stimulation interval should be changed according to changes in the return flow of blood.

As previously noted, the return flow of blood is an active function affected by the body's need for oxygen, but it can also be affected by e.g., heart rate. When a new stimulation rate is set after a change in the return flow of blood, this change in the stimulation rate can, by itself, also affect the return flow of blood. When this effect is determined, the heart stimulator can be devised so it automatically adapts the control of the stimulation interval to the changes in the return flow of blood.

In another embodiment of a heart stimulator, the control device controls the stimulation interval so it can only change within a predetermined range between a minimum stimulation interval and a maximum stimulation interval. As a result, the stimulation rate will be unable to drop below a lowest rate nor rise above an upper rate.

DESCRIPTION OF THE DRAWINGS

FIG. 2 shows a first embodiment of a heart stimulator according to the invention.

FIG. 3 is a block diagram showing the structure of the heart stimulator according to the first embodiment.

DESCRIPTION OF THE PREFERRED EMBODIMENTS

Figure 1:
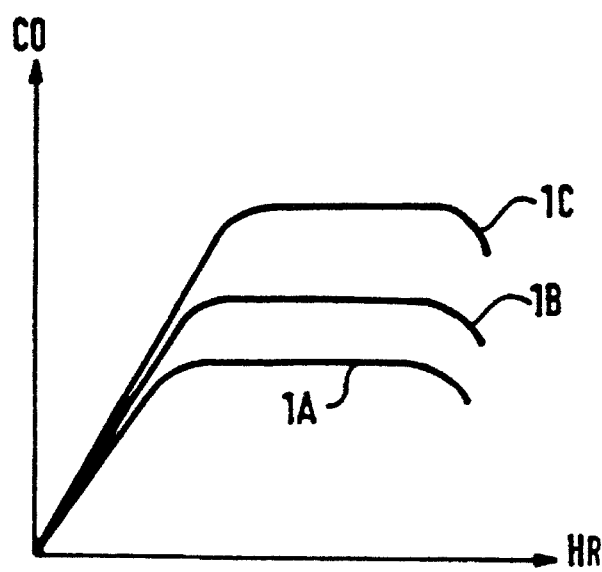
FIG. 1 is a diagram illustrating cardiac output at different levels of activity.

FIG. 1 shows a diagram in which one axis designates heart rate (HR) and the other axis designates cardiac output (CO). Three lines 1A, 1B and 1C in the diagram show how cardiac output changes with heart rate at three different levels of activity. Line 1A designates cardiac output at rest. As the figure shows, the increase in cardiac output is initially almost linear before flattening out at a threshold rate. Cardiac output will then remain almost constant at a plateau, even though the heart rate increases. This is caused by a decrease in stroke volume. The heart no longer has time enough to be completely refilled after each heart beat. When heart rate increases even further, cardiac output will decline rapidly, since the blood filling of the heart now becomes more severely impeded. Line 1B designates cardiac output at a first activity level. As the diagram shows, the plateau shifts toward a higher cardiac output and faster heart rate. Line 1C shows how an additional increase in the level of activity shifts the plateau additionally. Since cardiac output does not increase when rate increases at the plateau, the ideal heart rate is the rate at the transition to the plateau. At this rate, the heart will deliver maximum cardiac output for the activity level involved while the heart rate is the lowest possible, thereby reducing the load on the heart. Transition to the plateau for lines 1A, 1B and 1C physiologically corresponds to the situation in which the heart is just able to pump the blood flowing back to the heart through the veins. In other words, the heart does not impede the return flow by beating too slow nor does it impede the blood filling of the heart by beating too fast. When a person at rest becomes active, blood flow to the heart increases. An increased heart rate is then necessary to accommodate the increased flow. If the heart rate then increases too rapidly or to an excessively fast rate, blood flow will decline and heart rate slows. When the person's activity ceases, blood return declines, causing the heart rate to slow. If her/his heart rate slows too rapidly or too much, blood flow will increase, resulting in an increased heart rate. According to the invention, therefore, a heart is stimulated at a rate ideal for the individual's oxygen needs.

The heart stimulator 2 in FIG. 2 is connected to a heart 4. A tip electrode 6, placed in the apex of the right ventricle, is connected to the electronics section of the heart stimulator 2 by a first electrode conductor 8, and an indifferent electrode 10, placed in the superior vena cava, is connected to the electronics section of the heart stimulator 2 by a second electrode conductor 12. The heart stimulator 2 emits stimulation pulses via the tip electrode 6 and measures blood return to the heart 4 between the indifferent electrode 10 and the tip electrode 6.

FIG. 3 shows the heart stimulator 2 in a block diagram. The tip electrode 6 is connected by the first electrode conductor 8 to a pulse generator 14 via an output capacitor 16 and a first switch 18. When the first switch 18 is closed, the output capacitor 16 discharges through the tip electrode 6 across heart tissue and stimulates a heart contraction.

When the pulse generator 14 is to recharge the output capacitor 16, the first switch 18 opens and a second switch 20 closes. With the aid of the switches 18 and 20, charging and discharging of the output capacitor 16 can be performed without interfering with any other functions in the heart stimulator 2. A filter 22 and a detector 24 are also connected to the first electrode conductor 8 for sensing electrical signals in heart tissue. The detector signal is sent to a logic stage 26 in the heart stimulator 2. The logic stage 26 controls the switches 18 and 20 as well as the pulse generator's 14 charging of the output capacitor 16.

The logic section 26 communicates with a microprocessor 28 and, in conjunction therewith, a RAM 30.

A measurement device 32 is connected to the first electrode conductor 8 via a third switch 34 in order to measure blood flow into the heart 4. The third switch 34 makes it possible for the measurement device 32 to be enabled during an optional number of time periods in order to measure the return flow of blood. The measurement device 32 comprises an amplifier 36 whose positive input terminal is connected to a reference potential $U_{ref}$ and whose negative input terminal is connected to the switch 34. A first resistor 38 is connected to the output terminal of the amplifier 36, and a second resistor 40 is connected in parallel across the negative input terminal and the first resistor 38.

The measurement device 32 is connected to an A/D converter 42 which is connected, in turn, to the microprocessor 28. A value for the voltage obtained in measurement of the return flow of blood is generated in the microprocessor 28 and sent to a D/A converter 44. A measurement voltage is then sent, via the second electrode conductor 12, to the indifferent electrode 10.

When a voltage is applied across the indifferent electrode 10 and the tip electrode 6, the measurement device 32 will have, as an output signal, the compensated current required to keep the voltage constant across the indifferent electrode 10 and the tip electrode 6. Since voltage is a direct measure of current, the voltage is collected from the measurement device 32 via the A/D converter 42 and sent to the microprocessor 28 for determination of the return flow of blood.

The microprocessor 28 performs all the calculations necessary for checking and controlling the heart stimulator 2 according to changes in the return flow of blood. For example, measurement values can be compensated against previously stored maximum and minimum values for one or more preceding 24-hour period(s). The stored measurement values are kept in the RAM memory 30 and are successively replaced by new maximum and minimum values as (if) they occur. The microprocessor 28 can also determine the trend in changes in the stimulation interval and the return flow of blood over a number of heart beats. This can be used to affect the control of increases or decreases in future stimulation intervals. In addition, the microprocessor 28, on the basis of the minimum values, can determine a null point setting for the constant voltage across the indifferent electrode 10 and the tip electrode 6. Adjustment of the null point setting can be made, e.g., once every 24 hours.

In order to protect the electronics in the heart stimulator 2 from any defibrillation pulses which may be delivered to the heart 4, a first defibrillation protector 46 is connected to the first electrode conductor 8, and a second defibrillation protector 48 is connected to the second electrode conductor 12.

The heart stimulator 2 also contains a telemetry unit 50 which communicates with the logic stage 26 and which can telemetrically transmit information to an extracorporeal programming unit 52. It can also receive information and program changes from the latter unit.

Figure 4:
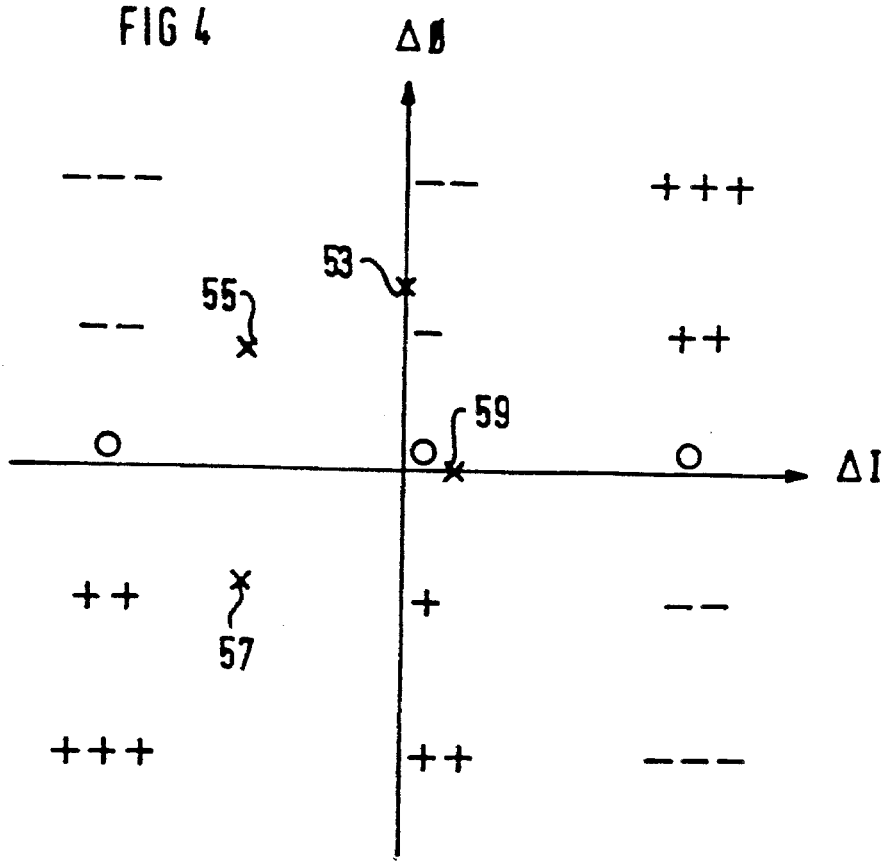
FIG. 4 is a diagram showing one possible principle for regulating the heart stimulator.

FIG. 4 shows a diagram depicting one possible principle according to which the microprocessor 28 can regulate the heart stimulator 2. The vertical axis designates changes in measured the return flow of blood (ΔΦ) and the horizontal axis designates the current change in the stimulation interval (ΔI). The change in the next stimulation interval can be read from the diagram. Reductions in the stimulation interval are designated with a minus sign and increases with a plus sign. The number of plus signs and minus signs respectively designates the magnitude of the increase or decrease respectively. Zero indicates that no change has occurred.

The change to be made in the stimulation interval can be stored in the RAM 30 and addressed by the microprocessor 28 with the respective value for the variable. The change can also exist in the form of an algorithm, the microprocessor 28 then calculating the change which shall be made in the stimulation interval. The heart stimulator 2 can also be devised so the microprocessor 28 can, on the basis of statistical data acquired over a long period of time, automatically make the necessary changes according to an identified change in the return flow of blood or a change made in the stimulation interval, respectively.

Various examples, each marked X, are shown in the diagram in FIG. 4. At the X designated 53, an increase in blood flow has occurred without any preceding change in the stimulation interval. The next stimulation interval will then decrease, i.e., the stimulation rate will increase. If the return flow of blood continues to increase, despite the shortening of the stimulation interval, as indicated at X 55 in the diagram, this means that the heart's cardiac output is inadequate for the body's needs, so the stimulation interval will again be shortened. If, on the other hand, the return flow of blood decreases when the stimulation interval, X 57, decreases, the next stimulation interval increases. When blood flow is constant, X 59, the stimulation interval does not change.

Figure 5:
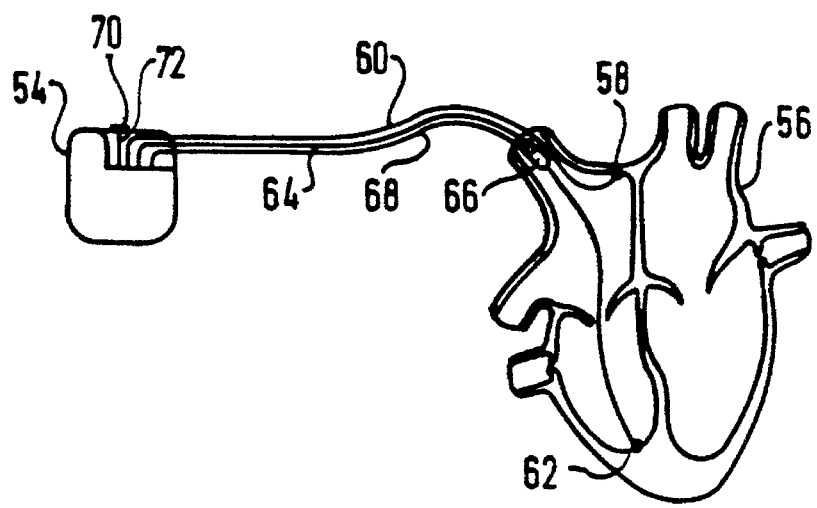
FIG. 5 shows a second embodiment of the heart stimulator according to the invention.

A second embodiment is shown in FIG. 5. A heart stimulator 54 is connected to a heart 56 with a first tip electrode 58 placed in the right atrium and a second tip electrode 62 placed in the apex of the right ventricle. The first tip electrode 58 is connected to the heart stimulator 54 via a first electrode conductor 60, and the second tip electrode 62 is connected to the heart stimulator 54 via a second electrode conductor 64. An indifferent electrode 66 is placed in the vena cava and connected to the heart stimulator 54 via a third electrode conductor 68. A measurement electrode 70 is arranged on the heart stimulator 54 and is connected to the electronics of the heart stimulator 54 via a fourth electrode conductor 72.

Figure 6:
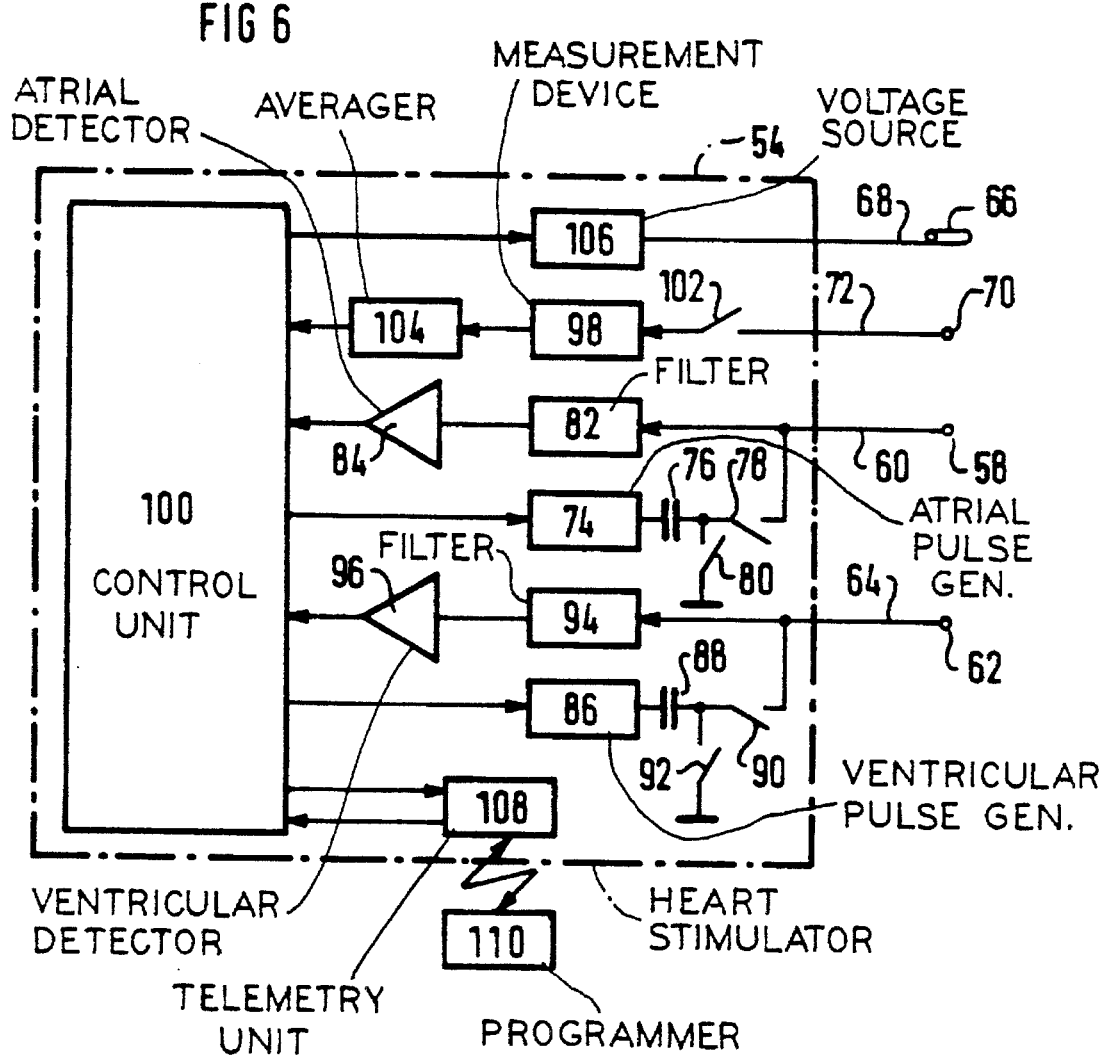
FIG. 6 is a block diagram showing the structure of the heart stimulator according to the second embodiment.

The block diagram in FIG. 6 provides a more detailed view of the structure of the heart stimulator 54. In the heart stimulator 54, an atrial pulse generator 74 is connected to the first tip electrode 58 via a first output capacitor 76, a first switch 78 and the first electrode conductor 60, in order to deliver stimulation pulses to the atrium. When the first switch 78 is closed, the first output capacitor 76 is discharged across atrial heart tissue. When the first output capacitor 76 is to be recharged, the first switch 78 opens and a second switch 80 closes. A first filter 82 and an atrial detector 84 are also connected to the first electrode conductor 60 to sense electrical signals in atrial heart tissue. In the corresponding manner, a ventricular pulse generator 86 is connected to the second tip electrode 62 via a second output capacitor 88, a third switch 90 and the second electrode conductor 64, in order to deliver stimulation pulses to ventricular heart tissue. A fourth switch 92 is enabled in the corresponding manner when the second output capacitor 88 is to be charged. A second filter 94 and a ventricular detector 96 are also connected to the second electrode conductor 64 to sense electrical signals in ventricular heart tissue.

A control unit 100 regulates the function of the pulse generators 74, 86 and the switches 78, 80, 90 and 92.

A measurement device 98 is connected to the measurement electrode 70 via a fifth switch 102 and the fourth electrode conductor 72. The measurement device 98 measures blood flow in the vena cava in the corresponding way described for the first embodiment according to FIGS. 2 and 3. An averager 104 is connected between the measurement device 98 and the control unit 100 to establish the average value for measured blood flow. A voltage source 106 supplies a constant voltage across the indifferent electrode 66 and the measurement electrode 70.

As in the previous embodiment, the pacemaker 54 has a telemetry unit 108 which communicates with the control unit 100 and which can telemetrically transmit and receive information and instructions from an extracorporeal programming unit 110.

In principle, the function of the pacemaker 54 is the same as in the first embodiment. In the embodiments of FIGS. 5 and 6, however, the atrium is also stimulated, so the heart stimulator 54 can synchronize the heart's pumping effect in a completely different way by even controlling the time elapsing between atrial stimulation pulses and ventricular stimulation pulses (the A–V interval) in order to further optimize the pumping function of the heart 56. In this instance, both the stimulation interval and the A–V interval are controlled by changes in the average value for measured return flow of blood. The control device 100 can also set refractory periods on the basis of changes in the average value for measured return flow of blood.

The invention is not limited to the embodiments described above. It can be implemented in unipolar, bipolar or multipolar heart stimulators which stimulate in either the atrium or ventricle or in both the atrium and ventricle, in defibrillators and cardioverters with a pacing capability etc. More-over, there can be variations in the regulatory principle without any departure from the invention's basic concept, i.e., to regulate the stimulation interval on the basis of changes in the return flow of blood to the heart. Here, measurement of the return flow of blood to the heart can be made at e.g., sites other than the vena cava.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator, for stimulating a heart having a return flow of blood comprising:

regulator means for regulating a variable function in said heart stimulator associated with stimulating said heart;

measurement means for measuring said return flow of blood to the heart and for generating an electrical signal exclusively corresponding thereto; and control means for generating a control signal dependent on said electrical signal for supply to said regulator means for controlling regulation of said variable directly and exclusively function dependent on said return flow of blood.

2. A heart stimulator as claimed in claim 1 wherein said means for measuring said return flow of blood includes first and second electrodes adapted to be disposed in said return flow of blood, and voltage supply means, connected across said first and second electrodes, for maintaining a constant voltage across said electrodes, said constant voltage resulting in a variable current being drawn by said voltage supply means for maintaining said constant voltage and said variable current comprising said electrical signal.

3. A heart stimulator as claimed in claim 1 wherein said regulator means comprises a pulse generator for generating and emitting stimulation pulses to said heart at a variable stimulation interval controlled by said control signal.

4. A heart stimulator as claimed in claim 1 further comprising:

averager means for determining an average value, from said electrical signal, of said return flow of blood, and wherein said control signal generated by said control means is dependent on said average value.

5. A heart stimulator as claimed in claim 4 wherein said averager comprises means for sampling a predetermined number of measured values represented by said electrical signal for the return flow of blood in each heart cycle, and means for determining said average value in a predetermined, preceding time interval from the predetermined number of sampled measured values.

6. A heart stimulator as claimed in claim 4 wherein said averager comprises means for sampling a predetermined number of measured values represented by said electrical signal for the return flow of blood in each heart cycle, and means for determining said average value in a predetermined number of preceding heart cycles from the predetermined number of sampled measured values.

7. A heart stimulator as claimed in claim 4 wherein said averager comprises means for determining a maximum value and a minimum value for said return flow of blood in each heart cycle, and means for determining said average value for a predetermined number of preceding heart cycles dependent on said maximum and minimum values.

8. A heart stimulator as claimed in claim 4 wherein said averager comprises means for determining said average value for a continuous measurement signal corresponding to said electrical signal for the return flow of blood for a predetermined preceding time interval.

9. A heart stimulator as claimed in claim 4 wherein said averager comprises means for determining said average value for a continuous measurement signal corresponding to said electrical signal for the return flow of blood for a predetermined preceding number of preceding heart cycles.

10. A heart stimulator as claimed in claim 1 further comprising:

a first tip electrode adapted for placement in an atrium of said heart;

a second tip electrode adapted for placement in a ventricle of said heart;

said regulator means comprises pulse generator means, connected to each of said first and second tip electrodes, for respectively emitting stimulation pulses to the atrium and to the ventricle; and said regulator means including timer means for setting a time interval between emission of an atrial stimulation pulse and emission of a ventricular stimulation pulse dependent on said control signal.

11. A heart stimulator as claimed in claim 1 further comprising:

means for monitoring changes in said electrical signal corresponding to the return flow of blood generated by said means for measuring and for identifying a momentary change in said electrical signal exceeding a predetermined threshold value as being abnormal and for preventing the electrical signal corresponding to said momentary change from contributing to said control signal.

12. A heart stimulator as claimed in claim 1 further comprising:

means for measuring at least one additional physiological variable, in addition to said return flow of blood, and wherein said control means comprises means for generating said control signal dependent on said return flow of blood and said at least one additional physiological variable.

13. A heart stimulator as claimed in claim 1 further comprising:

memory means for storing values representing the return flow of blood for a predetermined period of time.

14. A heart stimulator as claimed in claim 13 wherein said memory means comprises means for storing a minimum value and a maximum value of said return flow of blood for said predetermined period of time.

15. A heart stimulator as claimed in claim 1 further comprising:

a first tip electrode adapted for placement in an atrium of said heart;

a second tip electrode adapted for placement in a ventricle of said heart;

said regulator means comprises pulse generator means, connected to each of said first and second tip electrodes, for respectively emitting stimulation pulses to the atrium and to the ventricle;

said regulator means including timer means for setting a time interval between emission of an atrial stimulation pulse and emission of a ventricular stimulation pulse dependent on said control signal; and memory means for storing values representing a plurality of said time intervals occurring during a predetermined period of time and for storing values representing the return flow of blood for said predetermined period of time.

16. A heart stimulator as claimed in claim 15 wherein said control means comprises means for calculating, dependent on said stored values representing the return flow of blood and the time intervals, a correlation between changes in said return flow of blood and changes in said time interval, and for setting said control signal dependent on said calculation.

17. A heart stimulator as claimed in claim 16 wherein said control means includes means for limiting changes in said time interval set by said control signal to changes within a predetermined interval defined by a minimum time interval and a maximum time interval.

18. A heart stimulator as claimed in claim 1 further comprising:

- a first tip electrode adapted for placement in an atrium of said heart;
- a second tip electrode adapted for placement in a ventricle of said heart;
- said regulator means comprises pulse generator means, connected to each of said first and second tip electrodes, for respectively emitting stimulation pulses to the atrium and to the ventricle; and
- said regulator means including timer means for setting a time interval between emission of an atrial stimulation pulse and emission of a ventricular stimulation pulse dependent on said control signal.

memory means for storing values representing a maximum value and a minimum value among a plurality of said time intervals occurring during a predetermined period of time and for storing values representing the return flow of blood for said predetermined period of time.

19. A heart stimulator as claimed in claim 18 wherein said control means comprises means for calculating, dependent on said stored values representing the return flow of blood and the maximum value and the minimum value of said time intervals, a correlation between changes in said return flow of blood and changes in said time interval, and for setting said control signal dependent on said calculation.

20. A heart stimulator as claimed in claim 19 wherein said control means includes means for limiting changes in said time interval set by said control signal to changes within a predetermined interval defined by said minimum value and said maximum value.

* * * * *